United States Patent [19]

Miyota et al.

[11] Patent Number: 5,981,255

[45] Date of Patent: Nov. 9, 1999

[54] ALKALINE PROTEASE, PROCESS FOR THE PRODUCTION THEREOF, USE THEREOF, AND MICROORGANISM PRODUCING THE SAME

[75] Inventors: Yoshiaki Miyota; Shiro Fukuyama; Tadashi Yoneda, all of Chiba, Japan

[73] Assignee: Novo Nordisk A/S, Bagsvaerd, Denmark

[21] Appl. No.: 09/043,722

[22] PCT Filed: Nov. 1, 1996

[86] PCT No.: PCT/JP96/03216

§ 371 Date: Mar. 25, 1998

§ 102(e) Date: Mar. 25, 1998

[87] PCT Pub. No.: WO97/16541

PCT Pub. Date: May 9, 1997

[30] Foreign Application Priority Data

Nov. 2, 1995 [JP] Japan .................................. 7-308493

[51] Int. Cl.[6] ................................ C12N 9/54; C12N 1/20
[52] U.S. Cl. .................. 435/221; 435/252.5; 435/252.31
[58] Field of Search ............................... 435/221, 252.31, 435/252.5

[56] References Cited

U.S. PATENT DOCUMENTS

| | | | |
|---|---|---|---|
| 3,905,869 | 9/1975 | Hidaka et al. | 195/62 |
| 5,387,518 | 2/1995 | Sawayanagi et al. | 435/221 |

FOREIGN PATENT DOCUMENTS

| | | |
|---|---|---|
| 0510673 A2 | 10/1992 | European Pat. Off. . |
| 0571014 A1 | 11/1993 | European Pat. Off. . |
| WO 95/27049 | 10/1995 | European Pat. Off. . |
| 252949 | 10/1993 | Japan . |
| 78768 | 3/1994 | Japan . |
| 181760 | 7/1994 | Japan . |
| 163338 | 6/1995 | Japan . |
| 286194 | 10/1995 | Japan . |

*Primary Examiner*—Ponnathapura Achutamurthy
*Assistant Examiner*—Maryam Monshipouri
*Attorney, Agent, or Firm*—Steve T. Zelson, Esq.; Reza Green, Esq.

[57] ABSTRACT

The present invention provides a protease obtained from Bacillus, which is enzymatically active at alkaline pH and high temperature in the presence of surfactants. In a preferred embodiment, the protease is isolated from Bacillus sp. SD 114 and has a molecular weight of about 29,000 and a pI of about 10.

11 Claims, 7 Drawing Sheets

ALKALINE PROTEASE, PROCESS FOR THE PRODUCTION THEREOF, USE THEREOF, AND MICROORGANISM PRODUCING THE SAME

CROSS-REFERENCE TO RELATED APPLICATIONS

This application is a 35 U.S.C. 371 national application of PCT/JP96/03216 filed Nov. 1, 1996 and claims priority under 35 U.S.C. 119 of Japanese application 7-308493 filed Nov. 2, 1995, the contents of which are fully incorporated herein by reference.

TECHNICAL FIELD

This invention relates to a novel alkaline protease. More particularly, it relates to an alkaline protease which is stable in surfactants and heat resistant, its manufacturing method, its use in detergents, and microorganisms producing alkaline protease.

BACKGROUND ART

In recent years, environmental pollution has become a social issue. With regulation of the use of phosphate as an ingredient in detergents, an enzyme has been mixed with a detergent to improve detergency. Detergents with an enzyme such as protease, amylase, cellulase and lipase are currently marketed. Particularly, protease can degrade organic stains of clothes, 10 to 40% of which are caused by proteins and which cannot be cleaned with conventional detergents. Protease has become an essential ingredient improving detergency.

As protease for detergents, there are many enzymes originated from microorganisms which are active in the alkaline pH range, and proteases such as Kazusase (Showa Denko K. K.), Savinase (Novo), Maxacal (Gist), Alcalase (Novo) and Biosam (Showa Denko K. K.) have been used. With spreading of automatic dish washers, an enzyme usable for automatic dish washers is being required. Protease is effective on protein stains on dishes from egg yolk, dairy products, etc. However, generally inactivation of enzymes is accelerated in an aqueous solution at high temperature. Thus, an enzyme having an advantage in stability is required. Although Esperase (Novo), etc. have been currently used for this purpose, these enzymes do not have entirely satisfactory activity and stability. The protease which is known to be the most stable in surfactants at present is a protease produced by Bacillus strain SD 521 (patent application number 191781 of 1991). However, an even more stable protease is desired.

Therefore, the object of the present invention is to provide an alkaline protease more stable in the presence of a surfactant, manufacturing method of the alkaline protease, use of the protease for detergent, etc., and a microorganism producing the protease.

STATEMENT OF THE INVENTION

As a result of our devoted study, we found that protease API-26 produced by Bacillus sp. SD 114, a strain of Bacillus, has excellent stability and is suitable for detergent, and we completed the present invention.

Accordingly, the present invention provides a novel alkaline protease, its manufacturing method, its use, and a microorganism producing the protease.

1) Alkaline protease satisfying at least one of conditions specified in the following (a) to (c):
(a) Residual activity of more than 60% after 30 minutes at 40° C. in a surfactant solution (50 mM Atkins-Pantin borate buffer, pH 10, 0.1 mM EDTA, and 500 ppm of linear alkylbenzensulfonate LAS)
(b) Residual activity of more than 40% after 15 minutes at 55° C. in a buffer solution (50 mM Atkins-Pantin borate buffer, pH 10, and 0.1 mM EDTA)
(c) Residual activity of more than 20% after 15 minutes at 55° C. in a surfactant solution (50 mM Atkins-Pantin borate buffer, pH 10, 0.1 mM EDTA, and 500 ppm of LAS)
2) Alkaline protease specified in the above item 1) has the following properties:
(1) Action
  The protease hydrolyzes proteins and peptides.
(2) Optimal pH
  The optimal pH is approximately 12 when the protease is reacted with case in as a substrate at 30° C. for 10 minutes.
(3) Stable pH range
  The protease is stable at the pH range of 5 to 11 when it is incubated at 30° C. for 24 hours.
(4) Optimal temperature
  The optimal temperature is approximately 60° C. when the protease is reacted with casein as a substrate at pH 10 for 10 minutes.
(5) Molecular weight
  The molecular weight is 29,000±2,000 by SDS-polyacrylamide gel electrophoresis.
(6) Isoelectric point
  The isoelectric point is 10.1±0.5 by isoelectric focusing polyacrylamide gel electrophoresis.
3) Alkaline protease specified in either the above item 1) or 2) produced by microorganisms belonging to Bacillus.
4) Alkaline protease specified in the above item 3) produced by a microorganism belonging to Bacillus, which is Bacillus sp. SD 114 (FERM BP-5736).
5) Alkaline protease which has immunological cross-reactivity with protease specified in the above item 4), and satisfying at least one of the conditions specified in the following (a) to (c):
(a) Residual activity of more than 60% after 30 minutes at 40° C. in a surfactant solution (50 mM Atkins-Pantin borate buffer, pH 10, 0.1 mM EDTA, and 500 ppm of LAS)
(b) Residual activity of more than 40% after 15 minutes at 55° C. in a buffer solution (50 mM Atkins-Pantin borate buffer, pH 10, and 0.1 mM EDTA)
(c) Residual activity of more than 20% after 15 minutes at 55° C. in a surfactant solution (50 mM Atkins-Pantin borate buffer, pH 10, 0.1 mM EDTA, and 500 ppm of LAS)
6) Manufacturing method of alkaline protease characterized by obtaining the said protease from a culture where a microorganism belonging to Bacillus or its variant producing a protease specified in the above items 1) to 5)
7) Manufacturing method of alkaline protease specified in the above item 6) produced by a microorganism belonging to Bacillus, which is Bacillus sp. SD 114 (FERM BP-5736)
8) Bacillus sp. SD 114 (FERM BP-5736) and its mutants
9) Ingredients of the detergent in which the protease specified in the above items 1) to 5) is contained
10) Detergents in which the protease specified in the above item 1) to 5) is contained 11) Detergents for automatic dish washers in which the protease specified in the above items 1) to 5) is contained
12) Manufacturing method of peptides or amino acids characterized by reacting a protease specified in any of the above items 1) to 5) with protein or peptides

DETAILED DISCLOSURE OF THE INVENTION

Enzyme-producing microorganism

Figure 1:
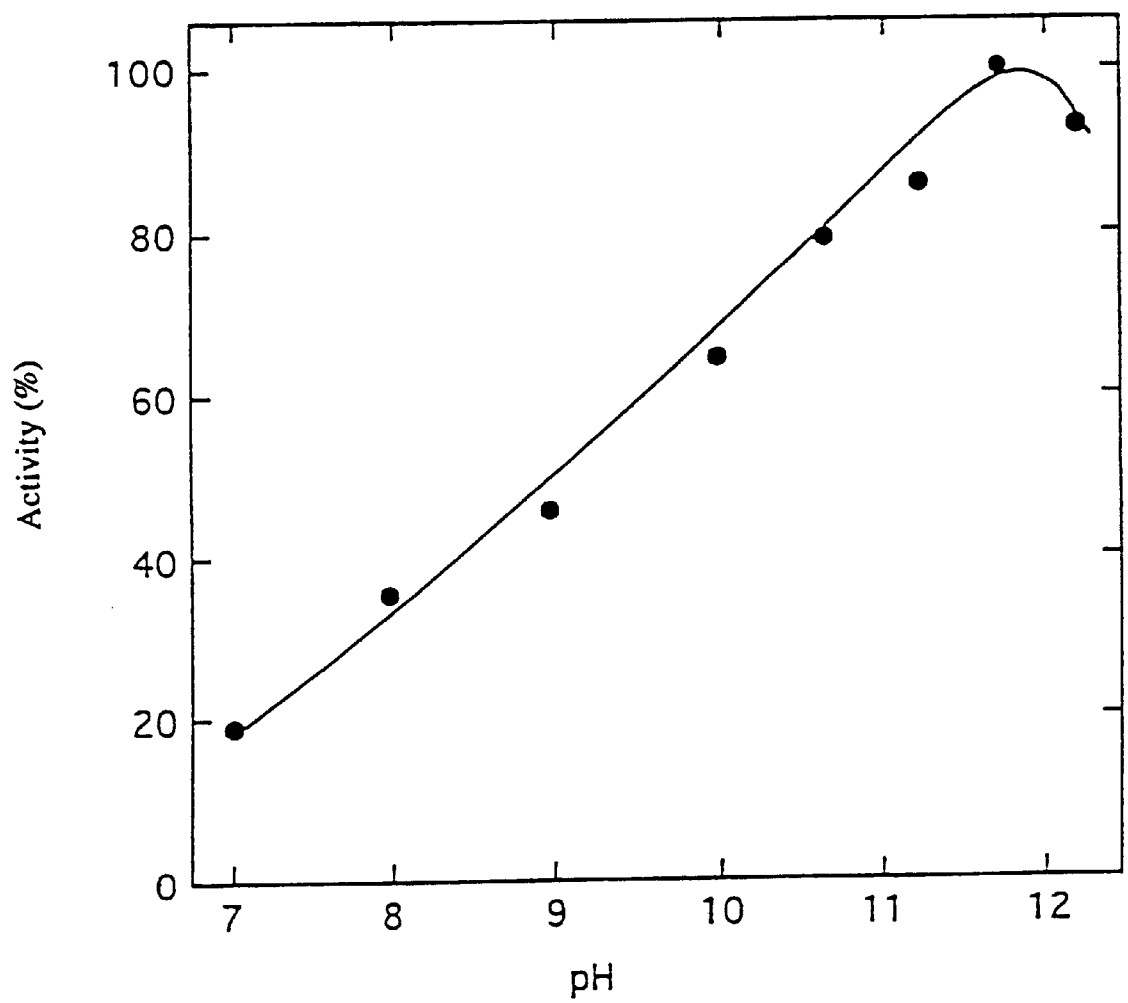
FIG. 1 Graph presenting the optimal pH range for the enzyme of the invention.

Bacillus sp. strain SD 114 which is one of microorganisms producing the enzyme of the invention is a strain closely related to Bacillus firmus bacteriologically. However, as it is apparently different in some properties from other known strains, it has been recognized as a new strain.

Bacteriological properties:

Bacillus sp. strain SD 114 related to this invention has the following bacteriological properties:
(a) Form: Bacilli
(b) Gram staining: Positive
(c) Sporogenesity: Positive
(d) Form of spores: Ellipse
(e) Mobility: Positive
(f) Attitude for oxygen: Aerobe
(g) Catalase production: Positive
(h) Growth in anaerobiotic condition: Negative
(i) Voges-Proskauer (VP) reaction: Negative
(j) pH of VP broth culture: 6.2
(k) Acid production: Glucose: Negative
   Arabinose: Negative
   Xylose: Negative
   Mannitol: Negative
(l) Aerogenesis from glucose: Negative
(m) Liquefaction of gelatin: Positive
(n) Degradation of starch: Positive
(o) Utilization of citrates: Negative
(p) Utilization of propionates: Negative
(q) Phenylalanine deamination: Negative
(r) Egg yolk reaction: Negative
(s) Reduction of nitrate: Negative
(t) Growth at pH 6.8: Positive
(u) Growth at pH 5.7: Positive
(v) Growth in 5% sodium chloride: Positive
(w) Growth in 7% sodium chloride: Positive
(x) Growth at 10° C.: Positive
(y) Growth at 30° C.: Positive
(z) Growth at 55° C.: Positive
(aa) GC content of microbial DNA (molar %): 45%

Referring to Bergey's Manual of Systematic Bacteriology, Vol. 2, William & Wilkins, 1986, systematic properties of this bacterium which has bacteriological properties specified by the above compared with other strains were as follows:

Bacillus sp. strain SD 114 related to this invention did not show the same specific properties as those of Bacillus firmus in acid production from sugar and growth at 50° C. However, the known strain SD 521 produces acid from glucose, deoxidizes nitrates, does not grow at pH 6.8, and does not grow at 50° C. NCIB 10309 produces acid from glucose. arabinose and mannitol. PB 92 produces acid from glucose and xylose, and can utilize propionates. It is obvious from the above bacteriological properties that this strain SD 114 is a mesophilic bacterium and Bacillus sp. closely related to Bacillus firmus, but it is different from the other known strains. Thus, this strain was recognized as a new strain. It has been deposited on $2^{nd}$ of October 1995 as FERM P-1 5214 at the National Institute of Bioscience and Human-Technology, Agency of Industrial Science and Technology (Domicile: 1–3, Higashi 1-chome, Tsukuba-shi, Ibaraki-ken, Japan), and transferred to International deposit under the Budapest Treaty on $30^{th}$ of October 1996 as strain SD 114 (FERM BP-5736).

In addition, protease productivity improved mutants which are obtained by spontaneous or induced mutation of the said strain SD 114, can be used as a bacterium producing the protease of the invention. In order to prepare these mutants, conventional methods can be used; for example, after inducing artificial mutation of the original strain by ultraviolet radiation or mutagens such as N-methyl-N'-nitro-N-nitrosoguanidine (NTG), the culture is inoculated into an agar medium containing skimmed milk, etc. A mutant with excellent productivity is selected from the colonies with a larger clear zone formed around colonies. Moreover, the productivity can be improved by utilizing a gene amplification phenomenon in the appropriate host cells transformed with a gene of the protease of the invention which is coupled together with an appropriate self-replicable DNA.

Manufacturing method of the protease

Any medium, where microorganisms producing the protease of the invention grows up and the protease is produced, can be used to manufacture the protease of the invention.

For example, glucose, maltose, sucrose, soluble starch, etc. are usable as the carbon source, and organic nitrogen compounds such as soybean cake, bran cake and corn steep liquid are usable as the nitrogen source. Besides, minerals such as phosphate, potassium salt and magnesium salt are added. In this invention, the culture is incubated under aerobic condition, for example, aeration culture or shake culture can be used. Incubation temperature is desirable to be 30 to 37° C. though a temperature between 20 and 40° C. is stable. It is desirable that the initial pH is 9 to 10 and pH during incubation is 8.5 to 10. Incubation period is 16 to 60 hours, and it is desirable to finish the incubation when the maximum protease activity is obtained. Purification of the culture obtained through the above can be performed according to conventional procedures for isolation and purification. The protease of the invention is obtained by salting out to precipitate protein, solvent fractionation method, spray drying method, lyophilization, etc. adding soluble salts or hydrophilic organic solvent to supernatant or filtrate obtained by centrifuging or filtration to remove body cells and solid residues of the medium. Moreover, the protease can be further purified by combination of other purification methods such as ion exchange chromatography and gel filtration chromatography. We named the protease of the invention obtained in the above manner as API-26. The activity of API-26 is assayed by the following method.

Assay of enzyme activity

Add 50 μl of the enzyme solution diluted appropriately to 500 μl of 50 mM Atkins-Pantin borate buffer, pH10, and pre-incubate at 30° C. for 3 to 5 minutes. To this solution, add 500 μl of 2% Hammarsten*s casein solution, pH 10, and after 10 minutes, stop the reaction by adding 2 ml of trichloroacetic acid (TCA) solution (0.032 M TCA solution adjusted to pH 4 with acetate buffer). Leave at 30° C. for more than 10 minutes, and filter with paper filter No.2 (Toyo Roshi). To 1 ml of filtrate add 5 ml of 0.4 M sodium carbonate and 1 ml of phenol reagent diluted 6-fold with water. Leave at 30° C. for 20 minutes for coloring, and then determine the absorbance at 660 nm. The unit of the protease activity is described by the katal. One katal is defined as the activity that the protease reacting with casein as a substrate at pH 10 and at 30° C. produces a degradation product with the absorbance at 660 nm equivalent to one mole of tyrosine.

Properties of the protease

Physical and chemical properties of the protease obtained by the invention are as follows:

(1) Action and substrate specificity

The protease degrades proteins or peptides such as casein, hemoglobin, albumin, meat protein, fish protein and soybean protein.

(2) Optimal pH

Determination of optimal pH:

Britton-Robinson broad buffer was used as a buffer solution. In order to determine the optimal pH, about 20 nkatal of the enzyme/ml were added to each pH buffer containing 1% casein. After incubating at 30° C. for 10 minutes, the enzyme activity was determined. As shown in Table 1 and FIG. 1 present the enzyme activity, where the activity at pH 11.7 is considered as 100. From these results, the optimal pH for this enzyme is around 12.

(3) Stable pH range

Figure 2:
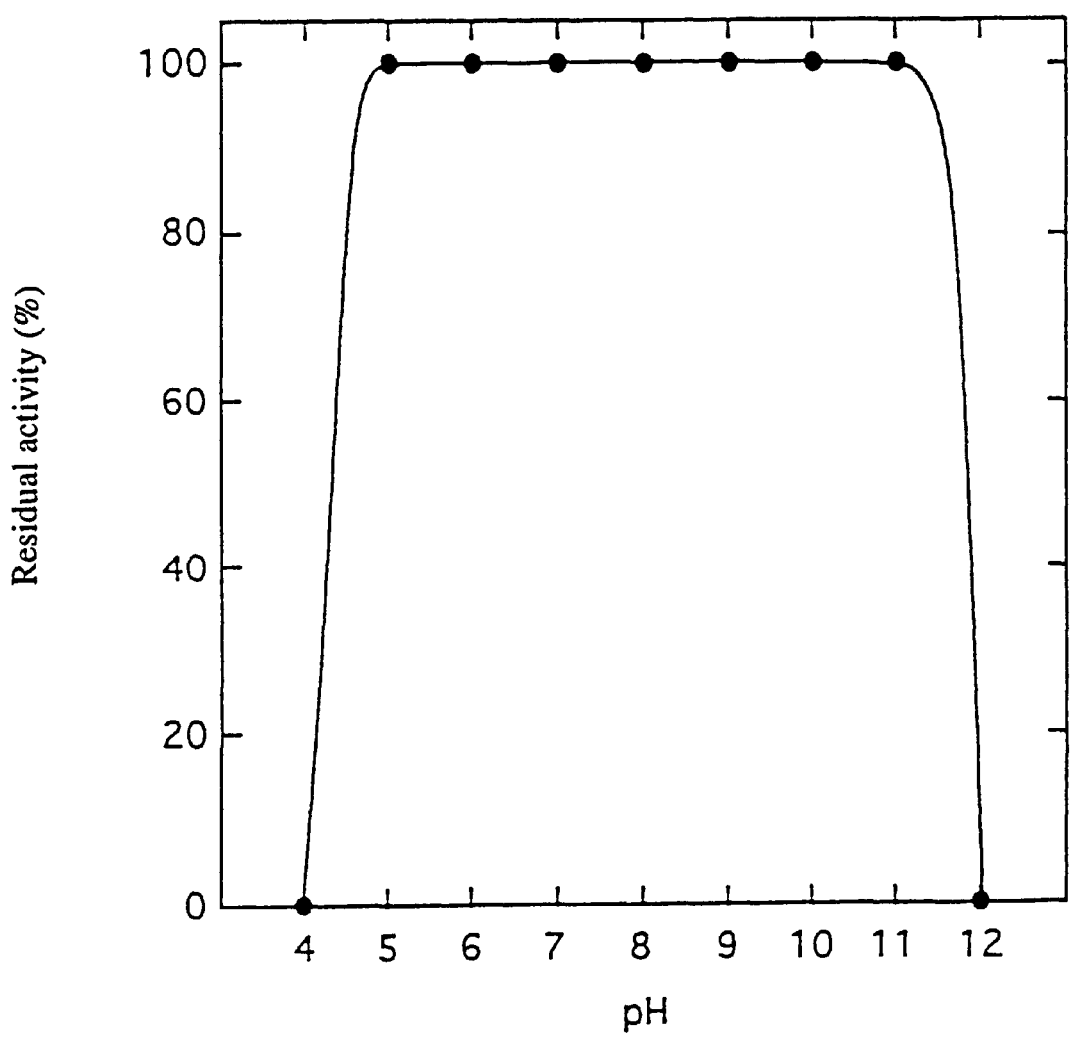
FIG. 2 Graph presenting the stable pH range for the enzyme of the invention.
Figure 3:
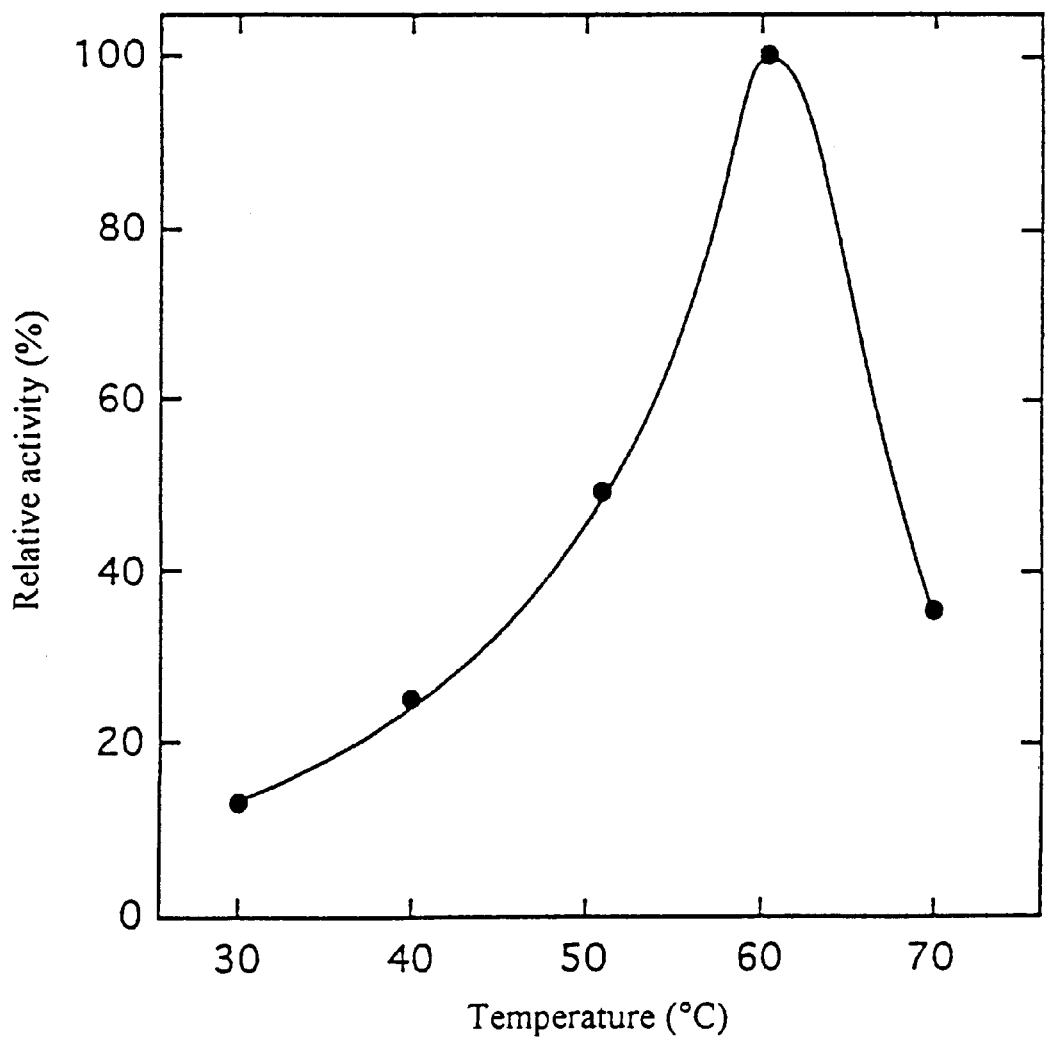
FIG. 3 Graph presenting the optimal temperature range for the enzyme of the invention.

Determination of stable pH range:

The enzyme was added at about 20 nkatal/ml to individual pH buffer solutions, and after incubating at 30° C. for 24 hours, the activity was determined. Table 2 and FIG. 2 present the residual activity, where the activity before incubation is considered as 100. From these results, the stable pH range of this enzyme is around 5 to 11 at 30° C.

TABLE 1

| Optimal pH for Activity | | | | | | | |
|---|---|---|---|---|---|---|---|
| pH | 7.1 | 7.9 | 9.0 | 9.9 | 10.6 | 11.2 | 11.7 | 12.1 |
| Activity | 19 | 35 | 46 | 64 | 79 | 86 | 100 | 94 |

TABLE 2

| Optimal pH for Stability | | | | | | | | |
|---|---|---|---|---|---|---|---|---|
| pH | 4 | 5 | 6 | 7 | 8 | 9 | 10 | 11 | 12 |
| Activity | 0 | 100 | 100 | 100 | 100 | 100 | 100 | 100 | 0 |

(4) Optimal temperature

Determination of optimal temperature:

After 25 mM Atkins-Pantin borate buffer, pH 10 containing 2 mM ethylenediaminetetraacetic acid (EDTA) was pre-incubated at each temperature, the enzyme was added and reacted for 10 minutes at each temperature. After the solution was incubated at 30° C. for 24 hours, the enzyme activity was determined. Table 2 and FIG. 2 present the relative activity, where the activity at 60° C. is considered as 100. From these results, the optimal temperature for this enzyme is around 60° C.

TABLE 3

| Optimal Temperature | | | | | |
|---|---|---|---|---|---|
| Temperature (° C.) | 30 | 40 | 50 | 60 | 70 |
| Activity | 13 | 25 | 49 | 100 | 35 |

(5) Effects of inhibitors

Effects of various inhibitors against this enzyme were investigated according to the following conditions and procedure:

A solution containing this enzyme at about 20 nkatal/ml in 50 mM borate buffer, pH 10 was prepared. To this solution, EDTA, p-mercuribenzoic acid (PCMV) or phenyl-methanesulfonyl fluoride (PMSF) was added at a concentration shown in Table 4. After incubating at 30° C. for 30 minutes, the enzyme activity was determined. The results are shown in Table 4 where the relative activity of the enzyme with no inhibitor is considered as 100%. As shown in Table 4, this enzyme is most intensively inhibited by PMSF, and accordingly, this enzyme is a serine protease.

TABLE 4

| Effect of Inhibitors | | |
|---|---|---|
| Inhibitor | Concentration | Activity |
| No inhibitor |  | 100 |
| PCMV | 1 mM | 100 |
| PMSF | 10 mM | 0.7 |
| EDTA | 5 mM | 99 |

(6) Molecular weight

The molecular weight of this enzyme was determined to be 29,000±2,000 by SDS-polyacrylamide gel electrophoresis.

(7) Isoelectric point

The isoelectric point is 10.1±0.5 by isoelectric focusing polyacrylamide gel electrophoresis.

(8) Stability

This enzyme satisfies at least one of the following conditions:

(a) Residual activity of more than 60% after 30 minutes at 40° C. in a surfactant solution (50 mM Atkins-Pantin borate buffer, pH 10, 0.1 mM EDTA, and 500 ppm of linear alkylbenzene sodium sulfonate (LAS)

(b) Residual activity of more than 40% after 15 minutes at 55° C. in a buffer solution (50 mM Atkins-Pantin borate buffer, pH 10, and 0.1 mM EDTA)

(c) Residual activity of more than 20% after 15 minutes at 55° C. in a surfactant solution (50 mM Atkins-Pantin borate buffer, pH 10, 0.1 mM EDTA, and 500 ppm of LAS)

Cross reactivity with anti-API-26 body

The protease of the invention preferably shows cross reaction with anti-API-26 body under the following condition for the determination.

Condition for determination of cross reaction:

The antigen API-26 is prepared at 2 mg/ml, and it is mixed with the equivalent quantity of Freund's complete adjuvant to make a complete water-in-oil emulsion. One ml of this emulsion is administered to two female rabbits on day 0, day 21, day 42 and day 63. Exsanguination with collection of all blood is carried out on day 70, and a serum sample containing the antibody is prepared.

The cross reaction is assessed with the Ouchterlony technique (Acta. Med. Scan. 133: 76–79, 1950), i.e.: the central well is filled with 10 μl API-26 or other proteases at a concentration of 1 mg/ml, and the surrounding wells are filled with 10 μl antiserum diluted at the proportion of the n power of 2 (n=1, 2, 3, 4, 5, 6 and 7). The plate is placed in a humid chamber and incubated at 37° C. overnight until precipitin lines are visible. If a precipitin line is formed at a 4-fold or more concentration of the minimum concentration at which the precipitin line for API-26 is formed, it is concluded that the enzyme has cross reactivity with anti-API-26 body.

Application of the protease

Peptides or amino acids can be produced by treating proteins or peptides with the protease of the invention. This protease can be used for processing object substances by treating object substances containing proteins or peptides with the protease. In the procedures used conventionally, the protease of the invention can be placed with the conventional proteases. Even under a severe condition where conventional enzymes are inactivated, the protease of the invention can be used as far as this protease is activated. For example, this protease is usable in the presence of LAS not only in the range of 50 ppm to 500 ppm but also at more than 500 ppm. However, it is preferable to use this protease at not more than 3,000 ppm, and more preferable to use it at not more than 300 ppm. This protease is usable at high temperature of more than 48° C. However, it is preferable to use this protease at less than 75° C., and more preferable to use it at less than 70° C.

Use

The alkaline protease of the invention is more highly stable in various detergent solutions or surfactants on the market than conventional alkaline proteases. As this protease is also stable against heat and it effectively degrades protein stains in warm water used for washing clothes or dishes, it is possible to increase detergency by mixing this protease in detergents.

Besides, this protease can be used for feed processing, food processing (fish oil processing, meat processing, etc.), fiber processing, wool processing, leather processing, washing of contact lenses, washing of pipe lines. In addition, this protease can be mixed with bath agents and depilatories.

Detergent compositions

This invention provides detergent compositions mixed with an alkaline protease with properties specified above. Although the quantity of the alkaline protease mixed with the detergent compositions of the invention is not limited, it is appropriate to mix a quantity equivalent to 10 to 1,000 nkatal per liter of the detergent solution. If the loading amount is too small, the detergency will not be improved satisfactorily. On the contrary, if the loading amount is too large, the detergency will not be improved as expected by the loading amount and it is not desirable from economical point of view.

The alkaline protease of present invention can be mixed with known detergent compositions without any change in the composition. Specific ingredients are not required for detergent compositions of the invention. Typical example of such detergent compositions is: detergent compositions with one or more types of composition consist of 10 to 50% by weight of a surfactant, 0 to 50% by weight of a builder, 1 to 50% by weight of an alkaline agent or mineral(s), and 0.1 to 5% by weight of an anti-redeposition agent, the enzyme, a bleaching agent, a fluorescent dye, an anti-caking agent and an anti-oxidant, based on the weight of the detergent composition.

The following surfactants usually contained in detergent compositions can be used: soaps, linear or branched alkyl or alkenyl sulfates, amidosulfates, aliphatic sulfated compounds such as alkyl or alkenyl ether sulfates with linear or branched alkyl group or alkenyl group where one or more out of ethylene oxide, propylene oxide and butylene oxide is added, alkyl sulfonates, amidosulfonates, dialkyl sulfosuccinate, aliphatic sulfonates such as sulfonates of α-olefin, vinylidene olefin and internal olefin, aromatic sufonates such as linear or branched alkyl benzene sulfonates, alkyl or alkenyl ether carboxylates or carboxylic amides with linear or branched alkyl group or alkenyl group where one or more out of ethylene oxide, propylene oxide and butylene oxide is added, α-sulfonic fatty acids or esters, amino acid type surfactants, alkyl or alkenyl acidic phosphate esters, phosphate ester surfactants such as alkyl or alkenyl phosphates, sulfonic acid type ampholytic surfactants, betaine type ampholytic surfactants, alkyl or alkenyl ethers or alcohols with linear or branched alkyl group where one or more out of ethylene oxide, propylene oxide and butylene oxide is added, polyoxyethylene alkylphenyl ethers with linear or branched alkyl group where one or more out of ethylene oxide, propylene oxide and butylene oxide is added, higher fatty acid alkanolamides or their alkylene oxide addition compounds, sucrose fatty acid esters, fatty acid monoesters of glycerin, alkyl or alkenyl amine oxides, tetraalkyl ammonium salt type cation surfactants, etc. A counter ion of anion surfactants is preferably a sodium ion or potassium ion. A mixture of one or more of these surfactants is contained in detergents.

The following inorganic compounds can be used as builders and alkalizers or inorganic electrolytes. As alkaline metal salts: phosphates such as orthophosphate, pyrophosphate, tripolyphosphate, metaphosphate, hexametaphosphate, phytates, etc.; phosphonic acid salts such as ethane-1,1-diphosphonic acid, ethane-1,1,2-triphosphonic acid, ethane-1-hydroxy-1,1-diphosphonic acid and their derivatives, ethanehydroxy-1,1,2-triphosphonic acid, ethane-1,2-dicarboxy-1,2-diphosphonic acid, methanehydroxyphosphonic acid, etc., phosphonocarboxylates such as 2-phosphonobutane-1,2-dicarboxylic acid, 1-phosphonobuthane 2,3,4-tridicarboxylic acid, α-methylphosphonosuccinic acid, etc., amino acid salts such as asparaginic acid, glutamic acid, etc., aminopolyacetates such as nitrilotriacetic acid, ethylenediamine tetraacetate, diethylenetriamine pentaacetate, etc., high molecular electrolytes such as polyacrylic acid, polyitaconic acid, polymaleic acid, anhydrous maleic acid copolymer, carboxymethyl cellulose salt, etc., non-dissociated polymers such as polyethylene glycol, polyvinyl alcohol, etc., carboxymethyl compounds such as diglycolic acid, oxydiglycolic acid, carboxymethyl oxysuccinic acid, citric acid, lactic acid, tartaric acid, sucrose, lactose, etc., organic acid salts such as carboxymethyl compounds of pentaerythritol, carboxymethyl compounds of gluconic acid, benzene polycarboxylic acid, oxalic acid, malic acid, oxydisuccinic acid, gluconic acid, etc., aluminosilicates such as zeolite, etc., inorganic salts such as carbonate, sesquicarbonate, sulfate, bisilicate, etc. as alkaline metal salts; starch, urea, etc. as organic compounds; sodium chloride, bentonite, etc. as inorganic compounds; and triethanolamine, diethanolamine, monoethanolamine, triisopropanolamine, etc as organic alkalizers.

As described above, detergent compositions of the invention contain a surfactant(s), alkaline protease of the invention and alkalizer or inorganic electrolytes as essential ingredients. Besides, as needed, ampholytic surfactants, bleachers such as sodium percarbonate, sodium perborate, etc., bleaching activators, dyes, builders, anti-redepositions such as polyethylene glycol, polyvinyl alcohol, polyvinyl pyrrolidone, carboxymethyl cellulose, etc., anti-caking agents, anti-oxidants, anticorrosives, fluorescent brightener, foaming boosters, other enzymes such as lipase, etc. can be included.

Any procedure may be used to mix the enzyme with the detergent compositions of the invention. However, it is not preferable to mix fine powder of the enzyme because of safety and health hazards of users of the detergent or workers in the detergent industry due to dust rising during handling of the detergent. Therefore, the enzyme is preferably formulated into a liquid or dust-free form. The form of the enzyme may be produced by any of conventional procedures such as tumbling granulation, extrusing granulation, fluidized bed granulation, and centrifugal fluidized bed granulation. The forms of the enzyme mixed with the detergent compositions of the invention are not limited to those produced according to these procedures. As the alkaline protease of the invention is highly stable, formulating of this enzyme can be performed at higher temperature than that by usual procedures for preparation, for example, at more than 50° C.

Exemplifications of the detergent compositions of the invention include laundry detergents containing the alkaline protease of the invention and detergents for automatic dish washers, etc.

The following are examples to illustrate the invention, but the invention is not limited to the following examples.

Detergents on the market specified in the examples were used. Before they were used, enzyme-free detergents were prepared by extracting enzyme granules contained in the detergents by sorting, etc.

EXAMPLE 1

Cultivation of Bacillus sp. Strain SD 114

Strain SD 114 was incubated with shaking at 35° C. for 66 hours in 300 ml containing 1% of casein, 1% of bouillon and 1% of polypeptone and adjusted at pH 7.5 with sodium carbonate, and then the enzyme was produced and secreted in the culture. This culture was centrifuged at 1000 G and 4° C. to obtain the supernatant. The activity of the enzyme in the supernatant was about 50 nkatal/ml.

EXAMPLE 2

Purification of Enzyme API-26

The supernatant of the culture obtained in Example 1 was filtered with a bacteria elimination membrane and then concentrated with an ultrafilter membrane. This concentrated solution was salted out with 30 to 60% saturated ammonium sulfate. The precipitate obtained was dissolved in 25 mM tris-hydrochloric acid buffer, pH 7.5 containing 1 mM $CaCl_2$, and dialyzed with the buffer. Then this solution was absorbed into the CM-cellulofine C-500 column (Seikagaku Corp.) at pH 7.5, and the enzyme was eluted with the concentration gradient method with 0 to 1 M KCl containing 1 mM $CaCl_2$. A fraction of the enzyme where the specific activity showed an about eight-fold increase compared with that before ion-exchange chromatography. The enzyme was detected as a single band by SDS- polyacrylamide gel electrophoresis of this fraction.

EXAMPLE 3

Temperature Stability

Figure 4:
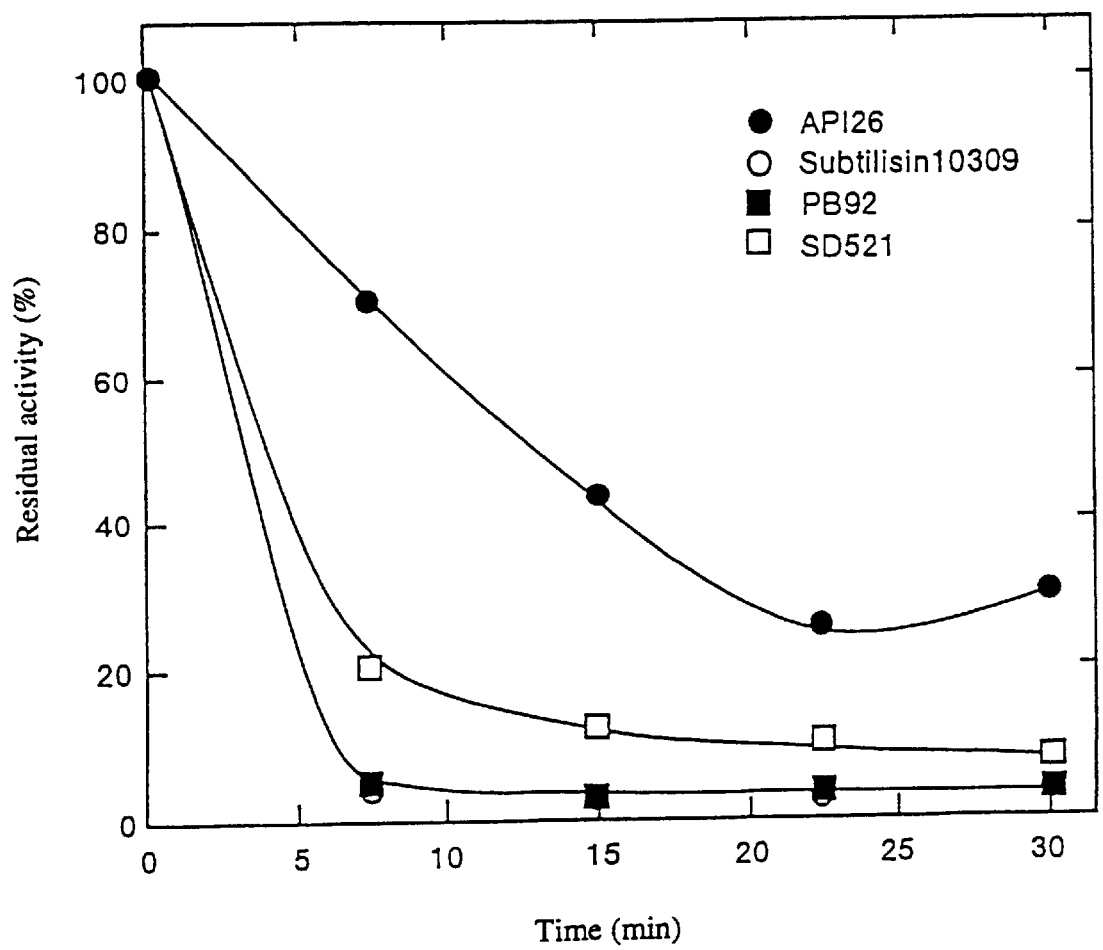
FIG. 4 Graph presenting the stability of the enzyme of the invention and known enzymes at 55° C.

Enzyme API-26 of the invention, Subtilisin 10309 (an enzyme produced by strain NCIB 10309), PB 92 (an enzyme produced by Bacillus strain PB 92) and SD 521 (an enzyme produced by Bacillus strain SD 521) were added to 50 mM Atkin-Pantin borate buffer, pH 10 containing 0.1 mM EDTA to make solutions with the activity of about 20 nkatal/ml. Incubating the solutions at 55° C., samples were collected periodically and the residual activity was determined at 30° C. Table 5 presents the residual activity at each time point where the activity at a condition without heat treatment is 100. Subtilisin 10309, PB 92 and SD 521 were prepared according to procedures specified in Patent Publication No. 8401 of 1976, Provisional Publication No. 125407 of 1976 and Provisional Publication No. 191781 of 1991, respectively. As shown in Table 5 and FIG. 4, API-26 has excellent temperature stability.

TABLE 5

| Temperature stability (55° C.) | | | | | |
|---|---|---|---|---|---|
| Time (min) | 0 | 7.5 | 15 | 22.5 | 30 |
| API-26 | 100 | 70 | 43 | 25 | 30 |
| Subtilisin 10309 | 100 | 4 | 3 | 3 | 3 |
| PB 92 | 100 | 5 | 3 | 4 | 3 |
| SD 521 | 100 | 20 | 13 | 10 | 8 |

EXAMPLE 4

Surfactant Stability

We studied the stability of this enzyme against surfactants.

Procedure of determination:

LAS was dissolved in 50 mM Atkin-Pantin borate buffer, pH 10 containing 0.1 mM EDTA to make a 500 ppm LAS solution. To this solution, enzymes (API-26, Subtilisin 10309, PB 92 and SD 521) were added to make solutions with the activity of about 20 nkatal/ml, and the solutions were incubated at 40° C. and 55° C. The residual activity was periodically determined at 30° C. Table 6 (40° C.) and Table 7 (55° C.) present the residual activity at each time point where the activity at time 0 is 100. As shown in these tables, API-26 has excellent stability in surfactants compared with conventional enzymes.

TABLE 6

| Stability in presence of a surfactant (40° C.) | | | | | |
|---|---|---|---|---|---|
| Time (min) | 0 | 7.5 | 15 | 22.5 | 30 |
| API-26 | 100 | 100 | 100 | 99 | 97 |
| Subtilisin 10309 | 100 | 0 | 0 | 0 | 0 |
| PB 92 | 100 | 0 | 0 | 0 | 0 |
| SD 521 | 100 | 7 | 5 | 0 | 0 |

TABLE 7

| Stability in presence of a surfactant (55) | | | | | |
|---|---|---|---|---|---|
| Time (min) | 0 | 7.5 | 15 | 22.5 | 30 |
| API-26 | 100 | 65 | 40 | 20 | 15 |
| Subtilisin 10309 | 100 | 0 | 0 | 0 | 0 |
| PB 92 | 100 | 0 | 0 | 0 | 0 |
| SD 521 | 100 | 3 | 0 | 0 | 0 |

EXAMPLE 5

Stability of Enzyme API-26 in Detergent Solutions

Figure 5:
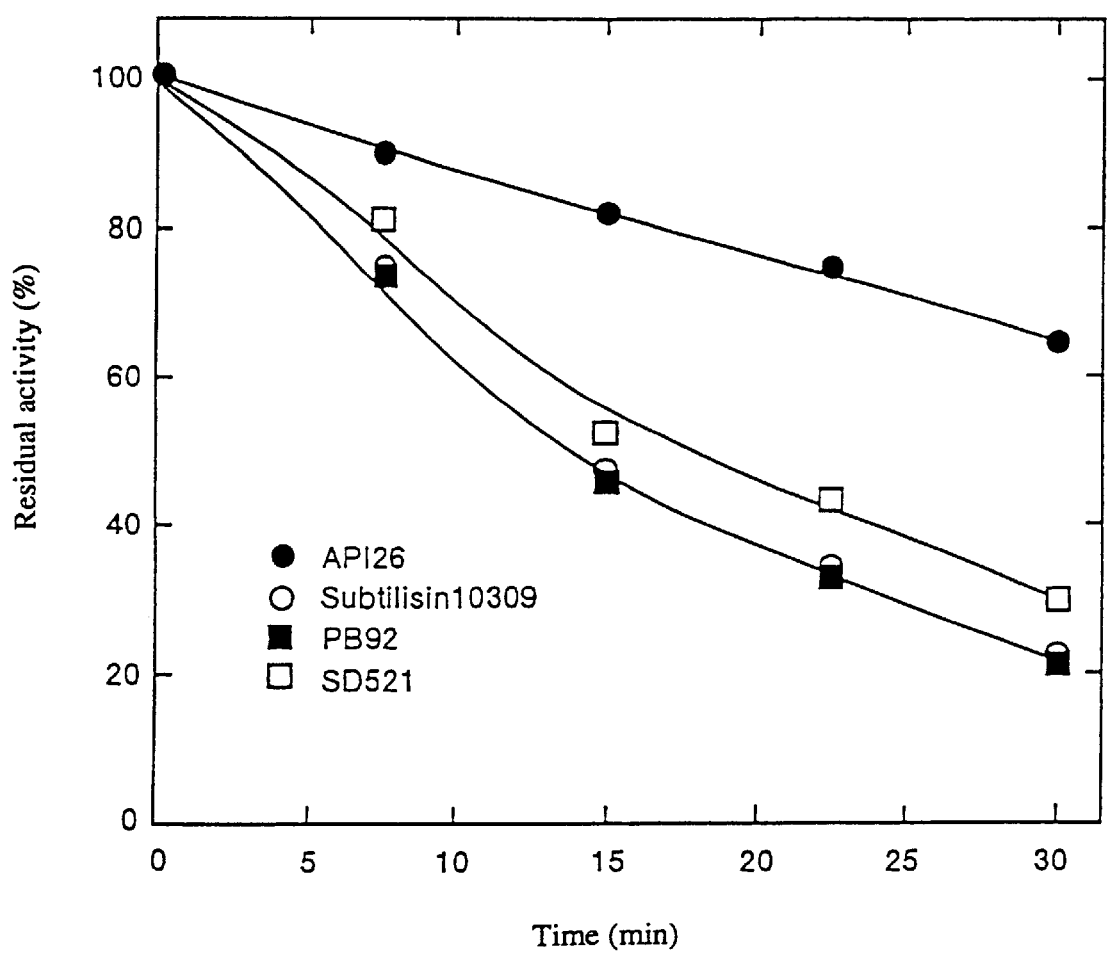
FIG. 5 Graph presenting the stability of the enzyme of the invention and known enzymes in a detergent on the market, Ultra Ariel, at 55° C.
Figure 6:
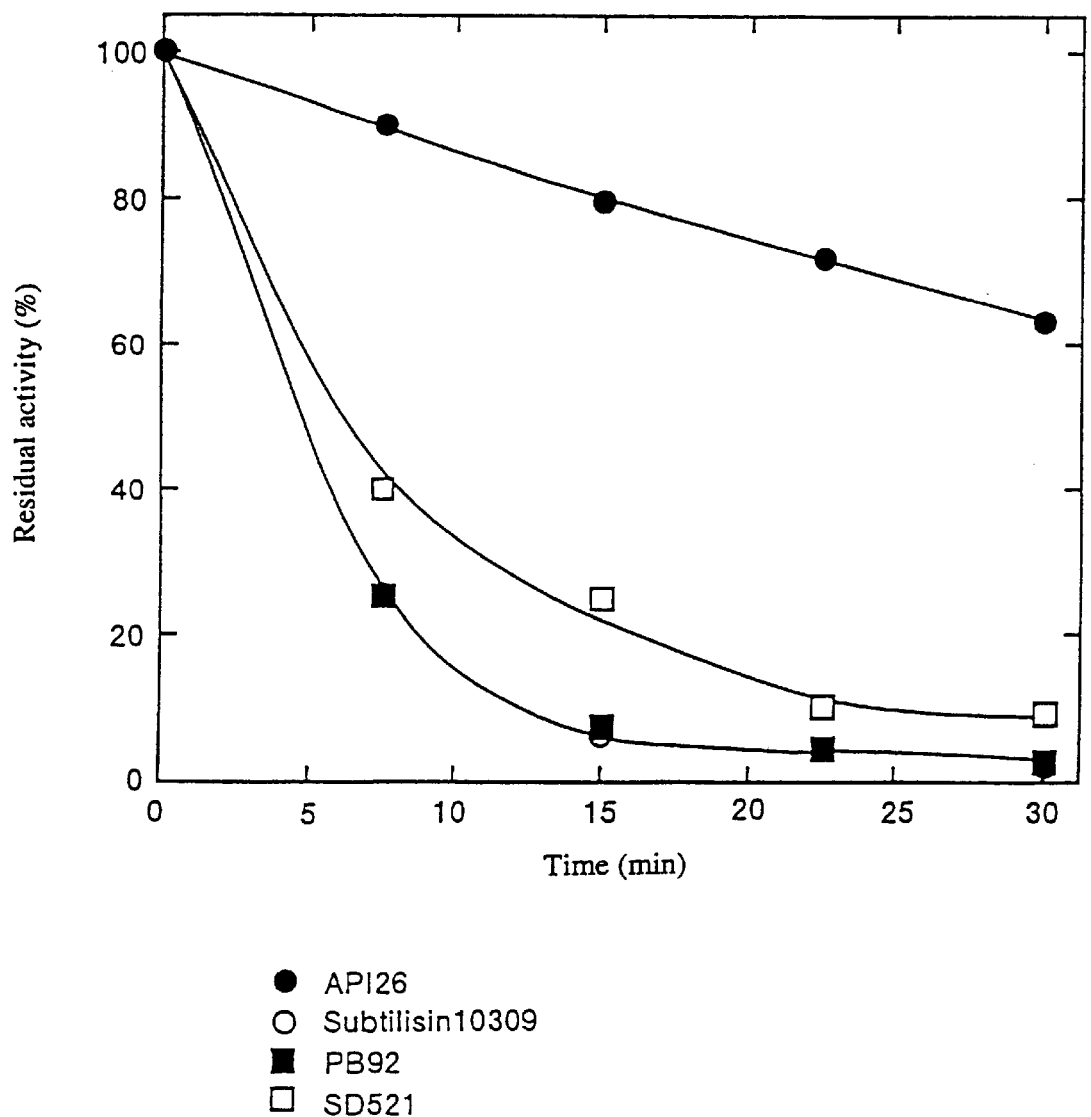
FIG. 6 Graph presenting the stability of the enzyme of the invention and known enzymes in a detergent on the market, Super Cheer, at 55° C.
Figure 7:
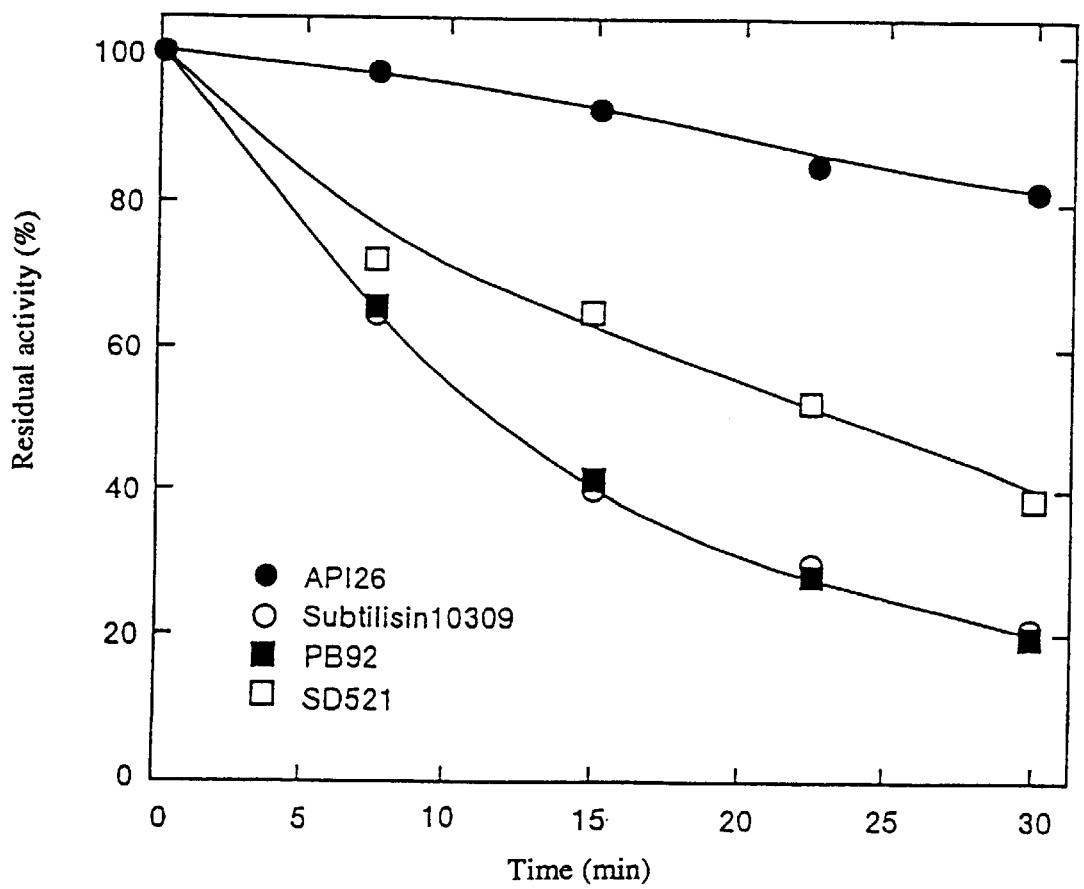
FIG. 7 Graph presenting the stability of the enzyme of the invention and known enzymes in a detergent on the market, Tide Grease Releasing, at 40° C.

We studied the stability of the invention in solutions of Ultra Ariel (P&G), Super Cheer (P&G) and Tide Grease Releasing (P&G) which are detergents on the market in accordance with the following conditions and methods. To 50 mM Atkin-Pantin borate buffer, pH 10 containing 1,000 ppm of $Ca^{2+}$ and 1,000 ppm of detergent solutions, the enzyme API-26 and other enzymes, Subtilisin 10309, PB92 and SD521, were added to make solutions with the activity of about 20 nkatal/ml, and the solutions were incubated at 55° C. or 40° C. The residual activity was periodically determined at 30° C. Tables 8 to 10 and FIGS. 5 to 7 present the residual activity at each time point where the activity at time 0 is 100. As shown in these tables and figures, API-26 has remarkably high stability in detergents compared with other enzymes.

TABLE 8

Ultra Ariel (55° C.)

| Time (min) | 0 | 7.5 | 15 | 22.5 | 30 |
|---|---|---|---|---|---|
| API-26 | 100 | 90 | 82 | 75 | 65 |
| Subtilisin 10309 | 100 | 75 | 48 | 35 | 22 |
| PB 92 | 100 | 73 | 46 | 33 | 21 |
| SD 521 | 100 | 81 | 53 | 44 | 31 |

TABLE 9

Super Cheer (55° C.)

| Time (min) | 0 | 7.5 | 15 | 22.5 | 30 |
|---|---|---|---|---|---|
| API-26 | 100 | 90 | 80 | 71 | 63 |
| Subtilisin 10309 | 100 | 25 | 7 | 5 | 3 |
| PB 92 | 100 | 26 | 8 | 5 | 4 |
| SD 521 | 100 | 41 | 25 | 10 | 9 |

TABLE 10

Tide Grease Releasing (40° C.)

| Time (min) | 0 | 7.5 | 15 | 22.5 | 30 |
|---|---|---|---|---|---|
| API-26 | 100 | 98 | 92 | 84 | 81 |
| Subtilisin 10309 | 100 | 65 | 40 | 30 | 21 |
| PB 92 | 100 | 66 | 41 | 28 | 20 |
| SD 521 | 100 | 72 | 66 | 52 | 39 |

EXAMPLE 6

Detergency Test of Detergents Containing Enzyme API-26

The supernatant of the culture obtained in the same manner as Example 1 was treated with a bacteria elimination membrane. After the supernatant was concentrated with an ultrafilter membrane, a crude enzyme was prepared by spray drying. The crude enzyme was added to Tide (P&G), a liquid detergent on the market, and the detergency was determined. The crude enzyme was added to Tide at a concentration of 100 nkatal/ml. The detergent containing the enzyme prepared was incubated at 40° C. for 4 weeks. Two grams of the detergent incubated for 4 weeks was added to 1 liter of water containing 40 ppm of calcium ion ($Ca^{2+}$) to wash stained clothes, and brightness was measured to determine the detergency defined by the following equation. Ten pieces each of EMPA-116 of a size of 5 cm×5 cm were used as stained clothes.

Detergency (%)=(Brightness of clothes after washing−Brightness of stained clothes)/(Brightness of unstained clothes−brightness of stained clothes)×100

Detergency was also tested with SD521 as control. The results are shown in Table 11. From the results, the addition of API-26 increase the effectiveness of liquid detergents.

TABLE 11

| Enzyme | Detergency (%) |
|---|---|
| API-26 | 62 |
| Subtilisin 10309 | 55 |
| PB 92 | 54 |
| SD 521 | 58 |
| Without enzyme | 52 |

EXAMPLE 7

Detergency Test of Detergents for Automatic Dish Washers with Enzyme API-26

We examined the detergency in an automatic dish washer using the crude enzyme specified in Example 6.

A detergent for automatic dish washers containing the enzyme was prepared with a detergent on the market, Hi-wash S (NCC) which contained polyethylene alkylen ether, sodium percarbonate, carbonate, sulfate and organic acid salt) mixed with the API-26 crude enzyme in a proportion of 20:1 by weight. This detergent was used at a concentration of 0.21% at washing, and the detergency was determined.

Washing condition

Machine: An automatic dish washer NP-600 assembled by Matsushita Electric Industrial Co., Ltd. where a detergent solution is injected from a rotating nozzle and dishes placed in the orbit of the injected detergent solution were washed.

Washing temperature: Gradually increased from 5° C. to 55° C.

Water: Hardness 3.5°DH

Concentration of enzyme: 0.01%

Amount of circulating water at washing: 2.5 liters

Stained dishes: Two porcelain dishes with a diameter of 25 cm were stained with 1 g of egg yolk and air-dried overnight.

Assessment of detergency

After washing, the area ($P_1$) of a purple color produced on the dishes with the amide-Schnitz solution reaction was measured with photographs. The cleaning rate was calculated from the stained area measured according to the following equation.

Cleaning rate (%)={$(P_0-P_1)/P_0$}×100 where $P_0$ is the area of the dish.

Table 12 shows the calculated cleaning rate. This test was also performed with SD521 as the control. The results showed that the detergent containing enzyme API-26 has a strong detergent action because the cleaning rate was 100% even for an obstinate stain such as egg yolk used in this test. It is considered that the enzyme highly contributes to improve the detergency of detergents for automatic dish washers.

TABLE 12

|  | Cleaning rate (%) |
|---|---|
| API-26 | 100 |
| SD 521 | 98 |
| No added enzyme | 80 |

POSSIBILITY OF INDUSTRIAL USE

The alkaline protease of the invention is highly stable in various detergents on the market or surfactants and also stable against heat compared with existing alkaline proteases. As this enzyme effectively degrades protein stains on laundry and dish washing, detergency can be increased by mixing with this enzyme.

Treating proteins or peptides with this enzyme, economical process of production of other peptides or amino acids is possible because the enzyme is stable.

Strain SD114 of Bacillus sp. of the invention and its mutants are mesophils easy to handle, which are useful for production of an alkaline protease of the invention.

An alkaline protease of the invention can be effectively produced by the manufacturing method of proteases of the invention where microorganisms belonging to Bacillus or its mutants are cultivated.

We claim:

1. An isolated protease derived from a Bacillus, wherein said protease:
   (i) has an optimal pH for enzymatic activity of about 12 when reacted with casein as a substrate at 30° C. for 10 minutes, and
   (ii) has at least one of the following properties:
   (a) Residual enzymatic activity of more than 60% after 30 minutes at 40° C. in a surfactant solution comprising 50 mM borate buffer, pH 10, 0.1 mM EDTA, and 500 ppm of linear alkylbenzenesulfonate (LAS);
   (b) Residual enzymatic activity of more than 40% after 15 minutes at 55° C. in a buffer solution comprising 50 mM borate buffer, pH 10, and 0.1 mM EDTA; or
   (c) Residual enzymatic activity of more than 20% after 15 minutes at 55° C. in a surfactant solution comprising 50 mM borate buffer, pH 10, 0.1 mM EDTA, and 500 ppm of LASD.

2. An isolated protease as defined in claim 1, wherein said protease:
   (i) is stable at the pH range of 5 to 11 when it is incubated at 30° C. for 24 hours;
   (ii) has an optimal temperature for enzymatic activity of approximately 60° C. when it is reacted with casein as a substrate at pH 10 for 10 minutes;
   (iii) has a molecular weight of 29,000±2,000 when measured by SDS-polyacrylamide gel electrophoresis; and
   (iv) has an isoelectric point of 10.1±0.5 when measured by isoelectric focusing polyacrylamide gel electrophoresis.

3. An isolated protease as defined in claim 1, wherein said Bacillus is Bacillus sp. SD 114 (Deposit No. FERM BP-5736).

4. An isolated protease which reacts by the Ouchterloney technique with a rabbit antibody raised against a protease as defined in claim 3.

5. A method for producing an alkaline protease as defined in claim 1, said method comprising (i) culturing a microorganism expressing said protease under conditions appropriate for said expression and (ii) recovering said protease from said culture.

6. A method as defined in claim 5, wherein said microorganism is Bacillus sp. SD 114 (FERM BP-5736).

7. An isolated bacterial culture comprising Bacillus sp. SD 114 (FERM BP-5736) or a bacterium derived therefrom, wherein said derived bacterium produces a protease as defined in claim 1.

8. A detergent comprising a protease as defined in claim 1.

9. A detergent as defined in claim 8, wherein said detergent is formulated for automatic dish washers.

10. A method for hydrolyzing a protein into peptides or amino acids said method comprising reacting said protein with a protease as defined in claim 1.

11. An isolated protease derived from Bacillus sp. SD 114, wherein said protease:
   (a) has a molecular weight of about 29,000 when measured by SDS-polyacrylamide gel electrophoresis; and
   (b) has an isoelectric point of about 10 when measured by isoelectric focusing polyacrylamide gel electrophoresis.

* * * * *